US006723855B2

(12) United States Patent
Avrutov et al.

(10) Patent No.: US 6,723,855 B2
(45) Date of Patent: Apr. 20, 2004

(54) METHOD FOR SYNTHESIZING LEFLUNOMIDE

(75) Inventors: Ilya Avrutov, Bat Hefer (IL); Neomi Gershon, Kfar Saba (IL); Anita Liberman, Ramat Aviv (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 40 days.

(21) Appl. No.: 09/779,928

(22) Filed: Feb. 8, 2001

(65) Prior Publication Data

US 2002/0022646 A1 Feb. 21, 2002

Related U.S. Application Data

(60) Provisional application No. 60/182,635, filed on Feb. 15, 2000.

(51) Int. Cl.[7] .............................................. C07D 261/18
(52) U.S. Cl. ...................................................... 548/248
(58) Field of Search .......................................... 548/248

(56) References Cited

U.S. PATENT DOCUMENTS

| 4,284,786 A | 8/1981 | Kåmmerer et al. |
| 4,892,963 A | 1/1990 | Gallagher et al. |
| 5,610,173 A | 3/1997 | Schwartz et al. |
| 5,783,592 A | 7/1998 | Schwartz et al. |
| 6,221,891 B1 * | 4/2001 | Faasch et al. ................ 514/378 |
| 6,303,792 B1 * | 10/2001 | Lau et al. ................... 548/248 |

FOREIGN PATENT DOCUMENTS

| EP | 0 013 376 A | 7/1980 |
| EP | 0 607 775 A | 7/1994 |

OTHER PUBLICATIONS

Doleschall, G., Seres, P., *J. Chem. Soc. Perkin Trans. I*, 1988, 1875–1879.
Fossa, P., Menozza, G., Schenone, P., *Il Farmaco*, 1991, 46, 789–802.

* cited by examiner

*Primary Examiner*—Robert Gerstl
(74) *Attorney, Agent, or Firm*—Kenyon & Kenyon

(57) ABSTRACT

A process for synthesizing leflunomide from 5-methylisoxazole-4-carboxylic acid and 4-trifluoromethylaniline is provided in which the carboxylic acid group of 5-methylisoxazole-4-carboxylic acid is chlorinated, forming 5-methylisoxazole-4-carboxylic acid chloride. The acid chloride is then reacted without intermediate distillation with 4-trifluoromethylaniline in the presence of an alkali metal or alkaline-earth metal bicarbonate acid scavenger.

26 Claims, No Drawings

METHOD FOR SYNTHESIZING LEFLUNOMIDE

This application claims the benefit of provisional application No. 60/182,635 filed Feb. 15, 2000.

FIELD OF THE INVENTION

The present invention relates to the anti-proliferative compound leflunomide and to a process for synthesizing leflunomide.

BACKGROUND OF THE INVENTION

Pyrimidine biosynthesis is an essential function of cells. It is the biosynthetic pathway to the DNA base constituents of uracil, cytosine and thymine and produces precursors of molecules used in the synthesis of ATP, several cofactors and other important cell components. Uracil, cytosine and thymine are essential to DNA replication during cell proliferation. [Prescott, L. M.; Harley, J. P.; Klein D. A. *Microbiology* 203 (4th ed., McGraw Hill, 1999)]. Many diseases are caused by or are aggravated by the failure of natural mechanisms to regulate cell proliferation, such as cancer and some inflammatory diseases like rheumatoid arthritis. Most cancer therapies attempt to suppress the proliferation of rapidly dividing cells. Disruption of the pyrimidine biosynthesis pathway is one way to suppress proliferation of rapidly dividing cells because the disruption interferes with the cell's ability to replicate DNA.

Pyrimidine biosynthesis is a series of enzymatically catalyzed processes that convert carbamoyl phosphate and aspartic acid into cytidine triphosphate. About midway along the pathway lies the conversion of dihydroorotic acid to orotic acid by the dehydroorotate dehydrogenase enzyme. Leflunomide, N-(4'-trifluoromethylphenyl)-5-methylisoxazole-4-carboxamide (I), disrupts pyrimidine biosynthesis by inhibiting this enzyme.

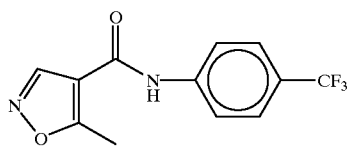

(I)

Leflunomide has been shown to be effective for treatment of the inflammatory disease rheumatoid arthritis although the mechanism by which it causes this particular therapeutic effect is not completely understood.

The first report of the anti-rheumatic property of leflunomide appeared in U.S. Pat. No. 4,284,786, which disclosed that leflunomide reduced symptoms of adjuvant arthritis in a rat model. This patent also reported that leflunomide may be prepared by reacting a 4-trifluoromethylaniline ("TFMA") with a 5-methylisoxazole-4-carboxylic acid ("MIA") derivative. In U.S. Pat. No. 4,284,786, Example (a1), 5-methylisoxazole-4-carboxylic acid chloride ("MIA-Cl") is reacted with two molar equivalents of TFMA in acetonitrile. This preparation is uneconomical on a large scale because acetonitrile is an expensive solvent.

TFMA is used as a scavenger of the HCl byproduct in the reaction of Example (a1). TFMA is too expensive to be used in this manner in a commercial process. We found that using triethyl amine ("Et$_3$N," pK$_b$=3.25) as an acid scavenger as described in Example (a3) of the '786 patent causes significant decomposition of leflunomide to N-(4-trifluoromethylphenyl)-2-cyano-3-hydroxycrotonamide ("HCA") of formula (II).

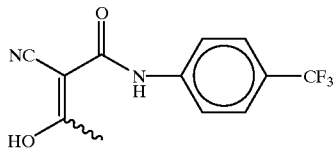

(II)

Although HCA is the active metabolite of leflunomide that forms in a patient's body, its presence in a pharmaceutical composition is problematic for accurate dosing and also affects other aspects of pharmaceutical processing. An alternative process for making leflunomide that is described in the '786 patent uses the Schotten-Baumann procedure to produce leflunomide with a minimum of contamination by HCA (Example a2 of the '786 patent). However, careful simultaneous addition of MIA-Cl and KOH is required for pH control. Any failure in the simultaneous delivery can lead to a rapid decomposition of leflunomide to HCA. A batch preparation which would not require the equipment, maintenance or sophisticated mechanical expertise for careful flow control would be preferable for a large scale commercial process for manufacturing leflunomide.

In addition to the problem of HCA formation, the production of substantially pure leflunomide is problematic because of the formation of byproducts derived from impurities in the starting materials. Two such impurities have chemical reactivities similar to MIA and TFMA and are carried through the process of the '786 patent to form byproducts that must be removed before the leflunomide can be used as an active ingredient in pharmaceutical. 3-Methyl-isoxazole-4-carboxylic acid is a common impurity in commercially available MIA. 3-Methyl-isoxazole-4-carboxylic acid originating in MIA is transformed by chlorination and reaction with TFMA to N-(4-trifluoromethylphenyl)-3-methyl-isoxazole-4-carboxamide (III). Another troublesome impurity in leflunomide derives from 4-methyl aniline, which is commonly present in minor amounts in TFMA obtained from commercial sources. 4-Methyl aniline forms 5-methyl-N-(4-methylphenyl)-isoxazole-4-carboxamide (IV) upon reaction with MIA-Cl.

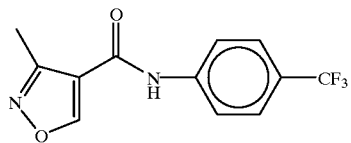

(III)

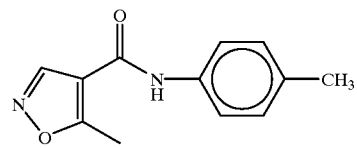

(IV)

It thus would be highly desirable to have available a process for preparing leflunomide substantially free of impurites (II), (III) and (IV) that could be conducted without careful reagent flow control and without costly solvents and bases.

The manufacture of the intermediate MIA-Cl in sufficient purity is also problematic for reasons other than the presence of impurities in the starting materials and the sensitivity of leflunomide to base-induced decomposition. According to a method disclosed in U.S. Pat. No. 4,892,963, Example 2(vi), MIA-Cl may be prepared by reacting MIA with thionyl chloride in the presence of N,N-dimethylformamide ("DMF") as a catalyst. It has been found that minor amounts of DMF left in the product after evaporation of excess thionyl chloride causes the MIA-Cl to discolor quickly. Discolored MIA-Cl produces leflunomide that is also discolored and too low in purity to be used as an active pharmaceutical ingredient. Additional purification steps are required to render the leflunomide pharmaceutically acceptable. Therefore, it is highly desirable that the MIA-Cl that is used to prepare leflunomide be as free as possible of DMF. High vacuum distillation is required to substantially remove high boiling DMF (bp=153° C. at 760 torr) from the MIA-Cl. The high vacuum (from 0.1 to 20 torr) required for that separation requires an additional investment in equipment. Further, it has been reported that even trace amounts of DMF remaining in the residue after high vacuum distillation can lead to discoloration of the obtained MIA-Cl and color problems with leflunomide.

MIA-Cl has been prepared without DMF as catalyst. [Doleschall, G.; Seres, P. *J. Chem. Soc. Perkin Trans. I*, 1988, 1875–1879]; [Fossa, P.; Menozzi, G.; Schenone, P. *Il Farmaco*, 1991, 46, 789–802]. However, high reaction temperatures and distillation of the resulting MIA-Cl were required. High reaction temperatures also can lead to discoloration of the MIA-Cl. Moreover, MIA-Cl can explode during distillation if the temperature is allowed to get to high. [Doleschall, et al., at p. 1877]. It therefore would also be highly desirable in a process for preparing leflunomide in high purity from MIA, via an MIA-Cl intermediate, that the MIA-Cl be formed under conditions that do not require that it be distilled before it is used to make leflunomide.

SUMMARY OF THE INVENTION

The present invention provides a practicable, economic process for preparing leflunomide in high yield, high purity and on a large scale from 5-methylisoxazole-4-carboxylic acid and 4-trifluoromethylaniline. The inventive process comprises the steps of chlorinating 5-methylisoxazole-4-carboxylic acid to form 5-methylisoxazole-4-carboxylic acid chloride, contacting the resulting 5-methylisoxazole-4-carboxylic acid chloride, without intermediate distillation, with 4-trifluoromethylaniline in the presence of an alkali metal or alkaline-earth metal bicarbonate and a solvent and crystalizing the leflunomide from the solvent. Suitable reaction solvents include water, ethyl acetate, toluene and dimethyl acetamide.

The present invention provides leflunomide substantially free of HCA and other impurities. The present invention further provides compositions and dosage forms for treating rheumatoid arthritis and other proliferative diseases that contain leflunomide made according to the present invention as well as methods of treating rheumatoid arthritis and other proliferative diseases with leflunomide.

DETAILED DESCRIPTION OF THE INVENTION

The present invention provides a practicable, economic process for synthesizing leflunomide in high yield, high purity and on a large scale. We have discovered an improved process for preparing leflunomide from the commercially available materials 5-methylisoxazole-4-carboxylic acid ("MIA") and 4-trifluoromethylaniline (Aldrich Cat. No. 22,493–6, 1998–1999). As described in Doleschall, G.; Seres, P. *J. Chem. Soc. Perkin Trans. I*, 1988, 1875–1879, MIA may be prepared by reacting ethyl acetoacetate, acetic anhydride, triethyl orthoformate to form ethyl ethoxymethyleneacetoacetate and reacting the product of that reaction with hydroxylamine hydrochloride and sodium acetate trihydrate.

The process of the present invention is represented schematically as follows and includes experimental aspects which are set forth in the accompanying detailed written description.

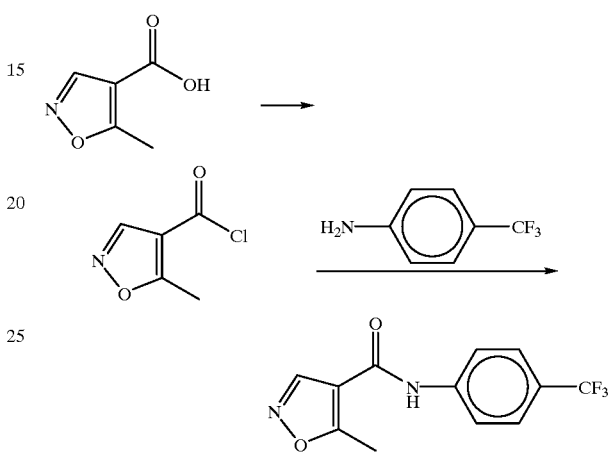

The process is a two step synthesis of leflunomide from 5-methylisoxazole-4-carboxylic acid and 4-trifluoromethyl aniline which does not require a distillation between the first and second step in order to purify the intermediate 5-methylisoxazole-4-carboxylic acid chloride ("MIA-Cl"). The leflunomide product of the second step can be precipitated from the reaction mixture in high purity. Although it may be desirable to further purify the leflunomide, leflunomide can be obtained in a pharmaceutically acceptable state of purity without further purification by using the method of this invention.

In the first step, the chlorinating step, MIA is contacted with a chlorinating agent to convert it to the corresponding acyl chloride, MIA-Cl. Those skilled in the art will appreciate that if the reaction of MIA with a chlorinating agent does not go to completion, it is necessary to distill MIA-Cl in order to separate it from unreacted MIA. Otherwise, the process will suffer a "double hit." Some of the MIA will not be converted to the necessary intermediate compound, MIA-Cl, resulting in a lower yield, and the unconverted MIA will compete for TFMA by forming a salt that renders the TFMA less reactive toward the MIA-Cl, which further lowers the yield. Therefore, the chlorinating reaction needs to go to substantial completion with or without a catalyst. It has been found that MIA can be converted to MIA-Cl in reasonable reaction times and at a lower temperature than by known methods without using DMF as a catalyst. The MIA-Cl produced according to the process of the present invention is suitable for use in the second step of the inventive process for synthesizing leflunomide, without distillation or other purification apart from evaporation of volatile substances.

The preferred chlorinating agent is thionyl chloride, $SOCl_2$, though other chlorinating agents may be used, such as oxalyl chloride, benzoyl chloride, $PCl_5$ or $PCl_3$. In the Examples that follow, thionyl chloride was used. The chlorinating agent is preferably used in 5 molar excess or greater.

MIA and the chlorinating agent may be contacted at room temperature in a vessel equipped with means for mechanically agitating (e.g. stirring), heating and evacuating the vessel. The order of addition of MIA and the chlorinating agent is not critical. Either before or after contacting, the temperature of the vessel is preferably raised to between about 40° C. and about 55° C., more preferably between about 45° C. and about 50° C. and the reaction mixture is preferably agitated at this temperature for an amount of time sufficient for completion of the reaction, typically 4 to 6 hours. The time required for complete reaction will depend upon temperature, the ratio of MIA to the chlorinating agent and solvent, if any. The MIA-Cl obtained after the reaction between MIA and the chlorinating agent is substantially complete is referred to hereinafter as "crude MIA-Cl."

Any excess chlorinating agent and volatile byproducts should be removed after the MIA has been substantially converted to MIA-Cl. Removal of the excess chlorinating agent and volatile byproducts is preferably conducted by evaporation under vacuum. Evaporation is preferably done at a pot temperature of 80° C. or less under a vacuum of about 50 torr or greater because these conditions do not evaporate MIA-Cl at a significant rate or require expensive high vacuum equipment.

The chlorinating step may be conducted either neat or in an inert chlorination solvent. An inert chlorination solvent is any solvent that does not react with thionyl chloride or MIA-Cl. Preferred inert chlorination solvents have a boiling point higher than 76° C., the boiling point of thionyl chloride, and can therefore function as a chaser during evaporation of excess thionyl chloride. Alternative preferred inert chlorination solvents may have a boiling point above or below 76° C. and form azeotropes with thionyl chloride. A particularly preferred inert chlorination solvent is toluene. When the chlorinating step is conducted in a solvent, the ratio of MIA to inert chlorination solvent is preferably from about 1:3 to about 1:10.

Evaporation of excess thionyl chloride and other byproducts tends to occur faster at a given temperature and pressure when the chlorination is performed in an inert chlorination solvent than when it is performed neat. For instance, at 80° C. and 55 torr, complete evaporation takes about 3 to 6 hours from a reaction mixture in toluene, much less than the 9–18 hours that may be required when no solvent is used. However, using a solvent tends to slow the chlorination reaction. A reaction performed in solvent can be accellerated by using a higher temperature (e.g. 78–80° C.). Although higher temperatures tend to cause discoloration when the chlorination is conducted neat, there is little or no discoloration when the reaction is conducted in toluene at the reflux temperature of thionyl chloride. Accordingly, the preferred temperature range for chlorinating MIA is from about 50° C. to about 80° C. when an inert chlorination solvent is used. The resulting MIA-Cl is suitable for use in the second, acylation, step of the invention without distillation. The contents remaining in the vessel after removal of any excess chlorinating agent or volatile byproducts is referred to hereinafter as "the residue."

In the second step, the acylation step, of the inventive process, the crude MIA-Cl or residue is contacted with TFMA. The acylation step produces HCl in addition to leflunomide. The HCl will tend to form a hydrochloride salt with unreacted TFMA, deactivating it toward nucleophilic addition to the acyl chloride functionality of MIA-Cl. An acid scavenger is therefore provided in order to prevent this deactivation.

The use of acid scavengers in acylation reactions that eliminate HCl is known to the art. Compounds such as leflunomide that are base sensitive may be decomposed by injudicious selection of an acid scavenger. In addition to discussing the use of NaOH and Et$_3$N as acid scavengers, U.S. Pat. No. 4,284,786 suggests the use of carbonates, alcoholates and amine bases like pyridine, picoline and quinoline, though the list is hardly exhaustive of the possibilities that may be tried. No examples of such processes are disclosed. We found that none of the bases mentioned were suited to making leflunomide that is free of significant contamination with HCA.

It has now been found that sodium bicarbonate (NaHCO$_3$) and other alkali metal and alkaline-earth metal (i.e. Groups I and II) bicarbonates are far superior acid scavengers to those suggested by the '786 patent. Particularly preferred acid scavengers are NaHCO$_3$ and potassium bicarbonate (KHCO$_3$), the most preferred being NaHCO$_3$.

The acylation step of the present invention is conducted in a solvent system rather than neat. The acylation solvent system may be a one-component system or a system of two or more components. The solvent components include water, esters (preferably ethyl acetate), aromatic hydrocarbons such as toluene and substituted and unsubstituted carboxamides such as N,N-dimethylacetamide. Accordingly, the acylation solvent system may include any of these components individually or in mixtures with each other and any other solvents whose presence does not significantly retard the reaction of MIA-Cl and TFMA. The preferred solvent components of the present invention are water, toluene and N,N-dimethylacetamide.

Water may be used alone advantageously because bicarbonates are generally soluble in water. However, dissolution of the bicarbonate is not an essential feature of this invention. For instance, sodium bicarbonate may scavenge HCl as a suspended solid or sediment in reactions conducted in ethyl acetate and toluene.

In the acylation step of the inventive process, the crude MIA-Cl or residue is contacted with TFMA in the presence of the above-described bicarbonates in the acylation solvent system. Preferably, the crude MIA-Cl or residue is added to a solution or suspension of TFMA and the bicarbonate in the acylation solvent system. The addition should be conducted at a temperature of from about 20° C. to about 65° C., more preferably about 40° C. to about 60° C. External heat may be applied to attain the desired temperature and, in addition, the exothermicity of the reaction may assist in achieving and/or maintaining the reaction temperature. The temperature of the reaction mixture should not be allowed to rise above about 65° C. When necessary, the temperature may be modulated by adjusting the rate of addition of MIA-Cl or by external cooling.

TFMA is preferably used in slight excess over MIA-Cl, preferably from 1 to 1.2 molar equivalents, more preferably about 1.05 molar equivalents.

The bicarbonate acid scavenger is also preferably used in only modest molar excess over MIA-Cl, preferably from about 1 to about 3 molar equivalents, more preferably about 1.0–1.5 molar equivalents, yet more preferably about 1.05 to about 1.2 molar equivalents and most preferably about 1.1 molar equivalents. Alkali metal and alkaline-earth metal bicarbonates typically have been used in large excess over the substrates of the reaction when they have been used as acid scavengers. It has been found that a large excess of bicarbonate is not required for acid scavenging in the reaction of MIA-Cl with TFMA.

The acylation step of the inventive process is preferably conducted in a relatively highly concentrated solution. One of the advantages of high concentration is the improved yield of leflunomide that is obtained when leflunomide is precipitated from the reaction mixture, as described below. Accordingly, the acylation is preferably conducted using from about 4 to about 14 ml of solvent per gram of MIA-Cl, more preferably from about 5 to about 7 ml of solvent per gram of MIA-Cl.

Progress of the acylation may be monitored by any of the methods known to the chemical arts such as thin layer chromatography, gas chromatography or HPLC chromatography.

Leflunomide can be isolated in high purity by precipitation from the acylation reaction mixture. To precipitate leflunomide, the reaction mixture should be allowed to cool, preferably to a temperature of between about 0° C. and about 25° C., most preferably about 25° C. or ambient temperature of the laboratory or facility. The reaction mixture also may be cooled to any temperature that does not solidify it. The precipitated leflunomide may then be separated by filtration, decantation and the like, preferably by filtration, and optionally washed and/or dried. Leflunomide obtained by crystallization from the reaction mixture is substantially free of HCA (II), N-(4-trifluoromethylphenyl)-3-methyl-isoxazole-4-carboxamide (III) and 5-methyl-N-(4-methylphenyl)-isoxazole-4-carboxamide (IV). Using the present inventive process, leflunomide can be obtained that contains HCA (II) in less than about 150 ppm, more preferably less than about 100 ppm and most preferably less than about 50 ppm.

Leflunomide also may be isolated by other methods known in the art. For example, it can be isolated by evaporation of volatile substances and chromatography of the residue or crystallization of leflunomide from the residue using an appropriate recrystallization solvent. Likewise, leflunomide also may be separated from other substances by extraction techniques.

The resulting leflunomide may be used directly or after further purification in pharmaceutical compositions and dosage forms as described, for instance, in commonly-assigned co-pending application Ser. No. 09/736,727, published as U.S. patent application Publication No. 2001/0031878, which is herein incorporated by reference in its entirety.

The leflunomide obtained by practice of the present invention is suitable for the treatment of autoimmune disease like rheumatoid arthritis, systemic lupus erythematosis and multiple sclerosis; psoriasis, atopic dermatitis, asthma, urticaria, rhinitis, uveitis, type II diabetes, liver fibrosis, cystic fibrosis, colitis, and cancers and acute immunological diseases such as sepsis, allergies, graft-versus-host disease and host-versus-graft disease. The leflunomide obtained by the presently claimed process may be presented to a patient in need of therapy in the form of a dosage. Dosage forms are made from pharmaceutical compositions. Pharmaceutical compositions may contain a pharmaceutically acceptable vehicle, i.e. one or more pharmaceutical excipients in addition to the leflunomide.

The pharmaceutical compositions of the present invention may have few or many excipients depending upon the release rate desired and the dosage form used. For example, pharmaceutical compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and dibasic calcium diphosphate and other diluents known to the pharmaceutical industry. Yet other suitable diluents include waxes, sugars and sugar alcohols like mannitol and sorbitol, lactose, lactose monohydrate and spray dried lactose, acrylate polymers and copolymers, as well as pectin, dextrin and gelatin. Such diluents may affect the rate of dissolution and absorption.

Other excipients include tablet binders, such as povidone, acacia gum, pregelatinized starch, sodium alginate, glucose and other binders used in wet and dry granulation and direct compression tableting processes. Excipients that may also be present in a solid composition further include disintegrants like sodium starch glycolate, crospovidone, low-substituted hydroxypropyl cellulose and others. Additional excipients include tableting lubricants like magnesium and calcium stearate, sodium stearyl fumarate and polyethylene glycol; flavorings; sweeteners; preservatives; pharmaceutically acceptable dyes; and glidants such as silicon dioxide and talc.

Whether used in pure form or in a composition, leflunomide obtained by the claimed process may be in the form of a powder, granules, aggregates or any other solid form. The leflunomide may also be used to prepare solid pharmaceutical compositions by blending, mixing, wet granulation, dry granulation or other methods.

The dosages may be adapted for administration to the patient by oral, buccal, parenteral, ophthalmic, rectal and transdermal routes. Oral dosages include tablets, pills, capsules, troches, sachets, suspensions, powders, lozenges, elixirs and the like. The leflunomide also may be administered as suppositories, ophthalmic ointments and suspensions, and parenteral suspensions. The most preferred route of administration of the leflunomide is oral.

Capsule dosages will contain the solid composition within a capsule which may be made of gelatin or other encapsulating material. Tablets and powders may be coated. Tablets and powders may be coated with an enteric coating. The enteric-coated powder forms may have coatings comprising phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Preferred oral dosages of the present invention contain from about 20 mg to about 100 mg of leflunomide obtained by the process of the present invention.

Having thus described the present invention with reference to certain preferred embodiments, the following examples are provided to further illustrate the inventive process for synthesizing leflunomide. One skilled in the art will recognize variations and substitutions in the methods as described and exemplified which do not depart from the spirit and scope of the invention.

EXAMPLES

Example 1

Preparations of 5-methylisoxazole-4-carboxylic acid chloride.

a) A mixture of 5-methylisoxazole-4-carboxylic acid (5 g, 39.4 mm) and $SOCl_2$ (15 ml, 205.8 mm) was stirred at 47.5±2.5° C. for 4 h. Excess SOCl$_2$ was then evaporated under low vacuum (50 torr) at 50° C. The pale yellow liquid residue (5.7 g) was more than 99% 5-methylisoxazole-4-carboxylic acid chloride by HPLC.

b) A mixture of 5-methylisoxazole-4-carboxylic acid (5 g, 39.4 mm), SOCl$_2$ (15 ml, 205.8 mm) and toluene (15 ml) was heated to 79±1° C. and stirred for about 4–5 h. Excess SOCl$_2$ and toluene were evaporated under vacuum (50 torr) at 70° C. to give the title compound (≧99% purity) as a pale yellow liquid residue identical to that of Example 1(a).

Example 2

Preparations of Leflunomide a) 4-Trifluoromethylaniline (5.75 g, 35.7 mm) was suspended in a solution of NaHCO$_3$ (3.16 g, 37.6 mm) in water (30 ml). The suspension was warmed to 50° C. and then rapid stirring was begun. 5-Methylisoxazole-4-carboxylic acid chloride prepared by the procedure of Example 1 (5 g, 34.4 mm) was added dropwise to the rapidly stirred suspension over 20 min. After cessation of the addition, the mixture was stirred for another 2 h. The mixture was then allowed to cool to ambient temperature and leflunomide was isolated as a white powder by filtration. Drying at 60° C. gave leflunomide (8.2 g, 88%) in 96% purity by HPLC analysis.

b) 4-Trifluoromethylaniline (5.75 g, 35.7 mm) was dissolved in a mixture of NaHCO$_3$ (3.16 g, 37.6 mm), toluene (70 ml) and water (15 ml). The mixture was heated to 60° C. and then 5-methylisoxazole-4-carboxylic acid chloride was added dropwise over about 20 min. After cessation of the addition, stirring was continued for another two hours. The mixture was allowed to cool and precipitated leflunomide was isolated as a white powder by filtration. The powder was dried at 60° C. until no change in mass was observed over a 24 hour period, at which point the white powder (8.2 g, 88%) was determined to be 99.5% leflunomide by HPLC analysis.

c) 4-Trifluoromethylaniline (5.75 g, 35.7 mm) was dissolved in a mixture of NaHCO$_3$ (3.16 g, 37.6 mm), N,N-dimethylacetamide (0.7 ml, 7.5 mm) and toluene (70 ml). The mixture was warmed to 40° C. and 5-methylisoxazole-4-carboxylic acid chloride (5 g, 34.4 mm) was added dropwise over 20 min. The mixture was stirred at this temperature for another 3 h. and then it was heated to reflux temperature. The hot mixture was washed with water (3×10 ml). The organic phase was allowed to cool to ambient temperature, which induced leflunomide to precipitate as a white powder. The powder was isolated by filtration and then dried at 60° C. to give leflunomide (8.0 g, 86%) in 99.5% purity.

We claim:

1. A process for preparing leflunomide comprising the steps of
   a) chlorinating 5-methylisoxazole-4-carboxylic acid by contacting it with a chlorinating agent thereby forming crude 5-methylisoxazole-4-carboxylic acid chloride,
   b) optionally evaporating excess chlorinating agent or volatile byproducts of the chlorination under reduced pressure, whereby evaporation leaves a residue of unevaporated material containing 5-methylisoxazole-4-carboxylic acid chloride,
   c) contacting the so-formed crude 5-methylisoxazole-4-carboxylic acid chloride or residue with 4-trifluoromethylaniline in the presence of an alkali metal or alkaline-earth metal bicarbonate in an acylation solvent system comprising at least one solvent component selected from the group consisting of water, ethyl acetate, toluene and dimethyl acetamide, and
   d) isolating the leflunomide.

2. The process of claim 1 wherein the chlorinating step is conducted in the absence of N,N-dimethylformamide.

3. The process of claim 1 wherein the chlorinating step is conducted in the absence of a catalyst.

4. The process of claim 1 wherein the chlorinating step is conducted neat at a temperature of from about 40° to about 55° C.

5. The process of claim 1 wherein 5-methylisoxazole-4-carboxylic acid is contacted with the chlorinating agent in an inert chlorination solvent at a temperature of from about 50° C. to about 80° C.

6. The process of claim 5 wherein the inert chlorination solvent is toluene.

7. The process of claim 1 wherein the chlorinating agent is selected from the group consisting of thionyl chloride, oxalyl chloride, benzoyl chloride, PCl$_5$ and PCl$_3$.

8. The process of claim 7 wherein the chlorinating agent is thionyl chloride.

9. The process of claim 1 wherein the at least one solvent component of the acylation solvent system is water.

10. The process of claim 1 wherein the acylation solvent system is a mixture of toluene and water.

11. The process of claim 1 wherein the acylation solvent system is a mixture of toluene and N,N-dimethyl acetamide.

12. The process of claim 1 wherein the crude 5-methylisoxazole-4-carboxylic acid chloride or residue is contacted with 4-trifluoromethylaniline at a temperature of from about 20° C. to about 65° C.

13. The process of claim 12 wherein the crude 5-methylisoxazole-4-carboxylic acid chloride or residue is contacted with 4-trifluoromethylaniline at a temperature of from about 40° C. to about 60° C.

14. The process of claim 1 wherein the crude 5-methylisoxazole-4-carboxylic acid chloride or residue is contacted with from about 1 to about 1.2 molar equivalents of 4-trifluoromethylaniline with respect to 5-methylisoxazole-4-carboxylic acid.

15. The process of claim 1 wherein the alkali metal or alkaline-earth metal bicarbonate is present in from about 1.05 to about 1.2 molar equivalents with respect to the 5-methylisoxazole-4-carboxylic acid chloride.

16. The process of claim 1 wherein contacting the crude 5-methylisoxazole-4-carboxylic acid chloride or residue with 4-trifluoromethylaniline is conducted at a concentration of from about 4 to about 14 volumes of the acylation solvent system per one weight part of 5-methylisoxazole-4-carboxylic acid chloride.

17. The process of claim 16 wherein contacting the crude 5-methylisoxazole-4-carboxylic acid chloride or residue with 4-trifluoromethylaniline is conducted at a concentration of from about 4 to about 14 volumes of the acylation solvent system per one weight part of 5-methylisoxazole-4-carboxylic acid chloride.

18. The process of claim 1 wherein the leflunomide is isolated by precipitation from the acylation solvent system.

19. The process of claim 18 wherein the leflunomide is precipitated at a temperature of from about 0° C. to about 25° C.

20. The process of claim 18 wherein the leflunomide obtained by precipitation is substantially free of N-(4-trifluoromethylphenyl)-2-cyano-3-hydroxycrotonamide.

21. The process of claim 20 wherein the leflunomide obtained by precipitation contains about 150 ppm or less of N-(4-trifluoromethylphenyl)-2-cyano-3-hydroxycrotonamide.

22. The process of claim 21 wherein the leflunomide obtained by precipitation contains about 100 ppm or less of N-(4-trifluoromethylphenyl)-2-cyano-3-hydroxycrotonamide.

23. The process of claim 22 wherein the leflunomide obtained by precipitation contains about 50 ppm or less of N-(4-trifluoromethylphenyl)-2-cyano-3-hydroxycrotonamide.

24. The process of claim 23 wherein the leflunomide obtained by precipitation contains about 10 ppm or less of N-(4-trifluoromethylphenyl)-2-cyano-3-hydroxycrotonamide.

25. The process of claim 18 wherein the leflunomide obtained by precipitation is substantially free of 5-methyl-N-(4-methylphenyl)-isoxazole-4-carboxamide.

26. The process of claim 18 wherein the leflunomide obtained by precipitation is substantially free of N-(4-trifluoromethylphenyl)-3-methyl-isoxazole-4-carboxamide.

* * * * *